United States Patent [19]

McCarthy

[11] Patent Number: 5,129,892
[45] Date of Patent: Jul. 14, 1992

[54] ANATOMICALLY DESIGNED, DISPOSABLE SPECIMEN CUP

[76] Inventor: Dennis S. McCarthy, 5802 Ariel, Houston, Tex. 77074

[21] Appl. No.: 625,558

[22] Filed: Dec. 11, 1990

Related U.S. Application Data

[63] Continuation-in-part of Ser. No. 463,282, Jan. 10, 1990, abandoned.

[51] Int. Cl.⁵ ............................ A61F 5/44; A61B 5/00
[52] U.S. Cl. ...................................... 604/329; 128/761
[58] Field of Search ............................... 604/329–331; 128/761, 760; 4/144.1–144.4; D24/121, 122; 220/213, 305; 215/DIG. 3

[56] References Cited

U.S. PATENT DOCUMENTS

| | | |
|---|---|---|
| 105,979 | 8/1870 | Price . |
| 2,776,691 | 1/1957 | Tupper .................... 220/305 |
| 3,329,973 | 7/1967 | Bobbe ..................... 4/144.4 |
| 3,335,714 | 8/1964 | Giesy ...................... 128/761 |
| 3,485,233 | 12/1969 | Cord . |
| 3,625,654 | 12/1971 | Van Duyne . |
| 3,629,873 | 12/1971 | Long ....................... 4/144.2 |
| 3,843,016 | 10/1974 | Bornhorst et al. ........... 220/305 |
| 4,569,090 | 2/1986 | Muller . |

*Primary Examiner*—Randall L. Green
*Assistant Examiner*—R. Clarke
*Attorney, Agent, or Firm*—Vaden, Eickenroht, Thompson, Boulware & Feather

[57] ABSTRACT

A reclosable urine collection and specimen container having an oval shape and a configuration for increased patient comfort and convenience including a rim around an opening forming the top thereof having concave surfaces formed therein for conforming to the contour of the external genitalia of a female patient from whom a urine specimen is to be collected. Also provided is a lid having an oval shape for closing the specimen container having a thickened portion with a cavity formed therein for interacting with an outward flare formed in the rim of the container to securely retain the lid thereto. The lid is formed in a curved configuration and the pitch of the flare in the rim of the cup is less at one end of the oval than at the other end of the cup, while the angle of the cavity in the lid which receives the flare therein when applied to the cup is the same at both ends of the lid.

10 Claims, 2 Drawing Sheets

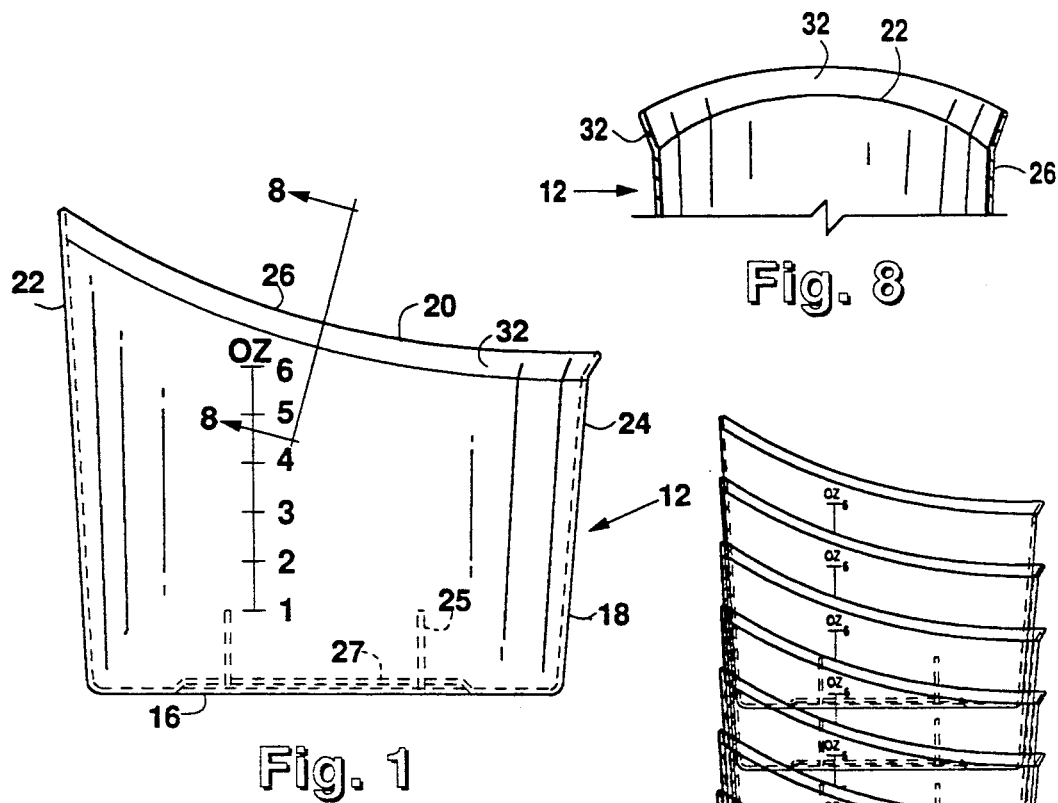
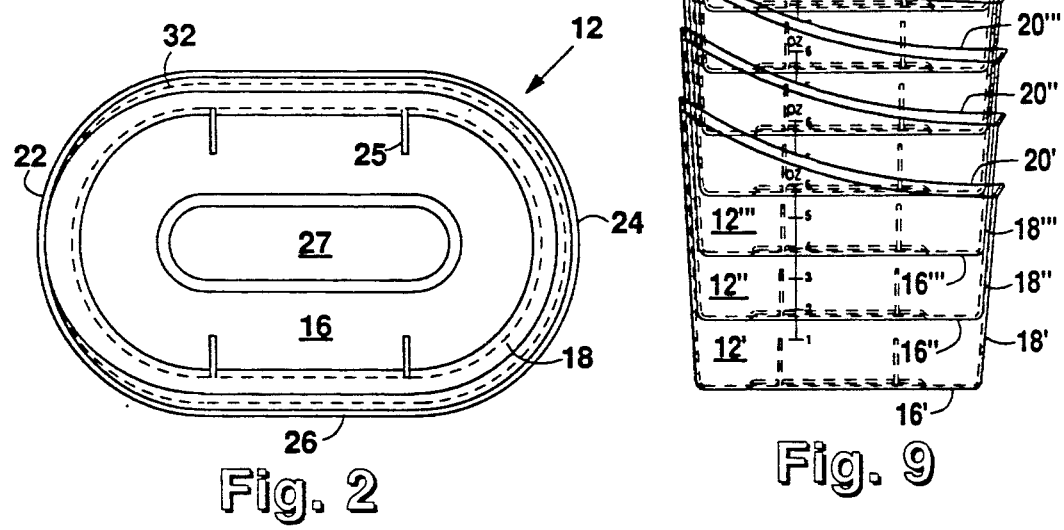
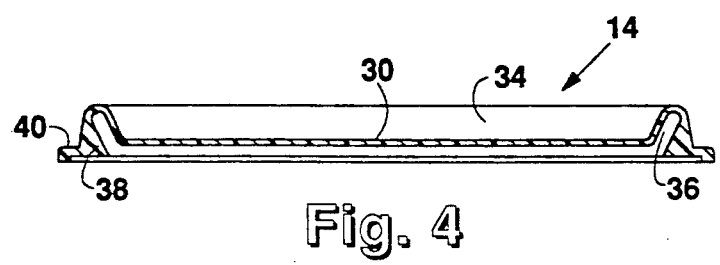

ANATOMICALLY DESIGNED, DISPOSABLE SPECIMEN CUP

CROSS REFERENCE TO RELATED APPLICATION

The present application is a continuation-in-part of my co-pending application Ser. No. 07/463,282, filed Jan. 10, 1990, now abandoned.

BACKGROUND OF THE INVENTION

The present invention relates to a urine collection and specimen container for use by female patients. More particularly, the present invention relates to a urine collection and specimen container having a concave rim for approximating the contour of the external genitalia of a female patient from whom a urine specimen is to be collected and a reclosable lid for that container which can be releasably secured thereto to close the container.

The patent literature includes multiple patents describing urine collection containers and/or cups ostensibly shaped so as to facilitate the collection of a urine specimen therein. Such cups need to be provided with an elongated dimension, when viewed from above, or otherwise shaped to prevent urine from contacting the patient's fingers or hand to increase sterility and decrease patient embarrassment because of the limited ability of female patients to control the direction in which urine is discharged. For instance, U.S. Pat. No. 3,485,233 discloses a female urine sampling device including a rim forming the upper edge of the sidewalls of a cup that is said to be shaped to fit against the vaginal area of the body of a woman. U.S. Pat. No. 3,329,973 discloses a disposable "urinal" which is tear-drop shaped when viewed from above. Further, U.S. Pat. No. 3,629,873 describes a cup with an upstanding sidewall shaped at its upper end to engage the female pubic region and receive within its opening the labial portion of the genitalia.

However, the devices described in those patents are characterized by a number of disadvantages and limitations. For instance, the device described in U.S. Pat. No. 3,485,233 does not have a reclosable lid, cannot be conveniently stacked for storage. The disposable "urinal" disclosed in U.S. Pat. No. 3,329,973 does not have a lid and is not, therefore, reclosable. Nor is that device suitable for use in the medical industry.

On information and belief, the device described in U.S. Pat. No. 3,629,873 is not likely to provide a tight fit between the lid and the cup. That patent describes a device having what appears to be threads on the cup and the lid, ostensibly for insuring a seal therebetween. However, if screw threads are used on that device, both lid and container must be round when viewed from above for the threads to be operable. As noted above, a round shape would decrease the ability of the device to conform to the shape of the external genitalia. Hence, that reference describes a bead formed in the lid which engages a groove in the cup, an arrangement which can be conveniently referred to as a snap ring. That snap ring is described in that reference as being "sufficiently secure" as to prevent spillage, but its location on the inside of the cup and the outside of the lid makes it unlikely that the necessary resiliency is present to provide for such a water-tight fit. In apparent recognition of that problem, a second embodiment of that device shown in the figures of that patent includes three such snap rings.

There is, therefore, a need for a reclosable specimen container which is anatomically designed in that it is provided with a concave rim for facilitating the collection of a urine specimen from a female patient which is inexpensive enough to manufacture as to be disposable and which provides a water-tight seal between the lid and the container. A principal object of the present invention is to provide such a specimen container.

As described below, a potential solution to the disadvantages of the devices described in these prior patents would be to provide a lid which is curved to fit against a curved, or concave, rim formed in the specimen container. However, curving the rim makes it difficult to obtain a water-tight seal between the rim and the lid, thereby making a water-tight seal less likely. To compensate for that difficulty requires tighter manufacturing tolerances between container and lid, and therefore, increased expense in making the mold necessary for forming the lid and specimen container of plastic or other suitable material. It is, therefore, another object of the present invention to provide a specimen container which solves those problems. Other objects, and the advantages of the present invention, will be made clear to those skilled in the art by the following description of a presently preferred embodiment of a urine collection and specimen container constructed in accordance with the invention.

SUMMARY OF THE INVENTION

These objects are achieved by providing a urine collection and specimen container for use by female patients which comprises an oval-shaped cup formed of a bottom and an upstanding sidewall surrounding the bottom, the sidewall terminating in a rim comprised of an outward flare having a variable pitch relative to the sidewall and forming an opening into the top of the cup. The sides of the rim are curved to approximate the contour of the external genitalia of a female patient from whom a urine specimen is to be collected. A resilient plastic lid is provided which is formed in a curve for fitting closely to the contoured rim of the cup. The lid is provided with a thickened portion having a cavity formed therein which receives the flare when the lid is applied to the rim of the cup. An elbow is formed in the thickened portion of the lid to bear against the outside surface of the flare to releasably secure the lid to the cup along the concave rim thereof for closing the cup and to provide a water-tight seal. The sidewall at one end of the oval-shaped cup is higher than the sidewall at the other end to further approximate the contour of the external genitalia, the concave portions of the rim being formed along the sides of the oval-shaped cup. The lid is also oval-shaped when viewed from above and the curve in the lid is formed along the sides of the oval, e.g., along the long axis of the lid.

BRIEF DESCRIPTION OF THE DRAWINGS

FIG. 1 is a side view of a preferred embodiment of the cup of a specimen container constructed in accordance with the teachings of the present invention.

FIG. 2 is a top, plan view of the cup of FIG. 1.

FIG. 4 is a sectional view of the lid of FIG. 3 taken along the lines 4—4 in FIG. 3.

FIG. 8 is a partial sectional view of the cup of FIG. 1 taken along the lines 8—8 in FIG. 1.

FIG. 9 is a side view of a plurality of cups of the type shown in FIG. 1 as they are nested for storage.

DETAILED DESCRIPTION OF THE PREFERRED EMBODIMENT

Figure 3:
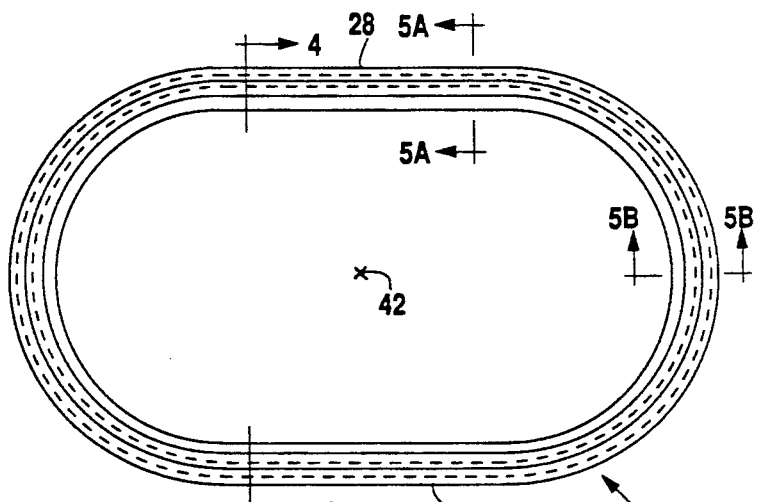
FIG. 3 is a bottom view of the lid for closing the cup of FIG. 1.

Referring now to the figures, there is shown a presently preferred embodiment of a specimen container which is comprised of a cup 12 (see FIGS. 1, 2, 7, and 8) and a lid 14 (see FIGS. 3–6). The cup 12 is formed of a bottom 16 having an upstanding sidewall 18 surrounding the bottom 16, the sidewall 18 terminating in a rim 20 forming an opening (not numbered) in the top of cup 12. When viewed from above (FIG. 2), the rim 20 of cup 12 is generally oval-shaped. The sidewall 18 at one end 22 of the oval-shaped cup 12 is higher than the sidewall 18 at the other end 24 of the oval (see FIG. 7, which is a side view of cup 12 looking from low end 24 to high end 22), and the portions of the rim 20 forming the sides of the oval-shaped cup 12 are curved to form concave surfaces 26 for closely approximating the contour of the external genitalia of a female patient (not shown) from whom a urine specimen is to be collected. The oval shape of cup 12, the high 22 and low 24 ends of the cup 12, and concave surfaces 26 all cooperate to conform cup 12 to the contours of the anatomy of the female patient to facilitate collection of the specimen without spillage.

As noted above, however, the concave surfaces 26 of the rim 20 of cup 12 along the sides of the oval makes the design of a lid which fits closely to the rim 20 which is reclosable and watertight difficult. These problems have been solved in the case of the present invention by providing a lid 14 as shown in FIGS. 3–6 which is oval-shaped when viewed from above (see FIG. 3) and which is formed in a curve along the length of the sides 28 of the oval (see FIG. 6) for fitting closely to the concave surfaces 26 of the rim 20 of cup 12. In other words, lid 14 is curved along the long axis of the oval.

As shown most clearly in FIGS. 2 and 8, the rim 20 of cup 12 is formed by a flare 32 having a variable pitch relative to the upstanding sidewall 18 of cup 12 depending upon whether reference is made to the ends 22 and 24 or sides 18 of the oval-shaped cup 12. In other words, there is a relatively low pitch to the flare 32 at the high end 22 of cup 12, e.g., the angle 33 between sidewall 18 and flare 32 is small, and a relatively high pitch to the flare 32 at the low end 24 of cup 12. As will be explained in more detail below, the pitch of flare 32 at the low end 24 of cup 12 is higher than at the high end 22 so as to keep the radius of the flare 32 on the rim 20 of the cup 12 at the low end 24 equal to the radius of the flare 32 on rim 20 at the high end 22. By comparison of FIGS. 1, 7, and 8, drawn roughly to scale, it can be seen that the pitch of flare 32, e.g., the angle between sidewall 18 and flare 32, along the sides 28 of the oval of cup 12 is intermediate, or in between, the low pitch of flare 32 at end 22 and the high pitch of flare 32 at end 24. More specifically, the angle 33 formed between the sidewall 18 and the flare 32 at the high end 22 of cup 12 is a greater obtuse angle relative to the sidewall 18 than the obtuse angle formed between sidewall 18 and flare 32 at the low end 24 of cup 12. Although drawn roughly to scale, it is not intended that the present invention be so limited. The purpose of the variable pitch flare 32 will be made clear below.

Figure 5A:
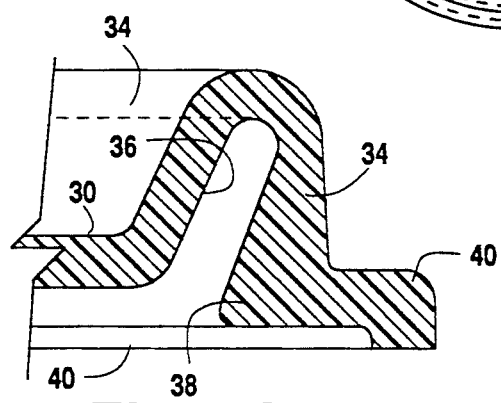
FIGS. 5A and 5B are enlarged sectional views through portions of the lid of FIG. 3 taken along the respective lines 5A—5A and 5B—5B in FIG. 3.
Figure 5B:
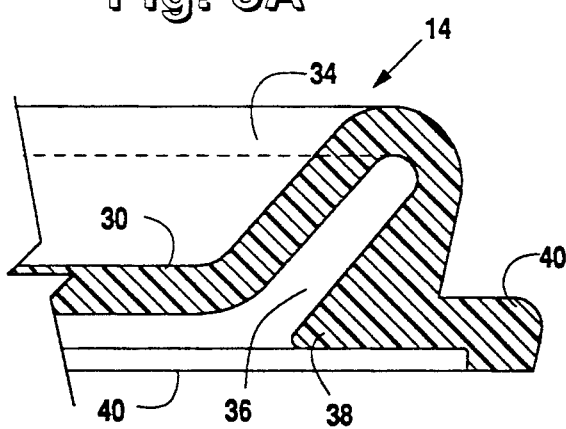

Referring to FIGS. 5A and 5B, lid 14 is comprised of a recessed interior portion 30 forming a flat surface for covering the cup 12 and an enlarged, or thickened portion 34 formed integrally therewith and encircling the lid 14. A cavity 36 is formed in the thickened portion 34 for receiving the rim 20 of cup 12 when lid 14 is applied to rim 20. The outward pitch of the flare 32 formed on the rim 20 of cup 12 (see FIG. 1) enables the lid 14 to releasably snap onto cup 12 along the concave surface 26 of rim 20 (see FIG. 2) as well as at the ends 22 and 24 for closing cup 12. For purposes of clarity, some of the structural details of lid 14 shown in FIGS. 5A and 5B are not shown in FIGS. 4 and 6. When snapped onto the rim 20 of cup 12, the elbow 38 of the thickened portion 34 of lid 14 helps insure a water-tight seal along the rim 26 of cup 12 when lid 14 is applied thereto by bearing against the outside surface of the flare 32 of cup 12 with equal pressure all the way around the opening of cup 12.

A flange 40 (see FIG. 5B) is formed in the lid 14 outside of the enlarged portion 34 thereof to serve as a stripper ring for facilitating removal of the lid 14 from the mold in which it is formed. In addition to providing the necessary depth to lid 14 to allow the forming of cavity 36 therein, the thickened portion 34 of lid 14, and especially the elbow 38 comprising a portion thereof, forms a rib along both sides of the long axis of the oval-shaped lid 14 which, when the lid 14 is removed from the mold, serves to hold the oval-shaped lid 14 in the curve along the long axis thereof as shown in FIG. 6.

Figure 6:
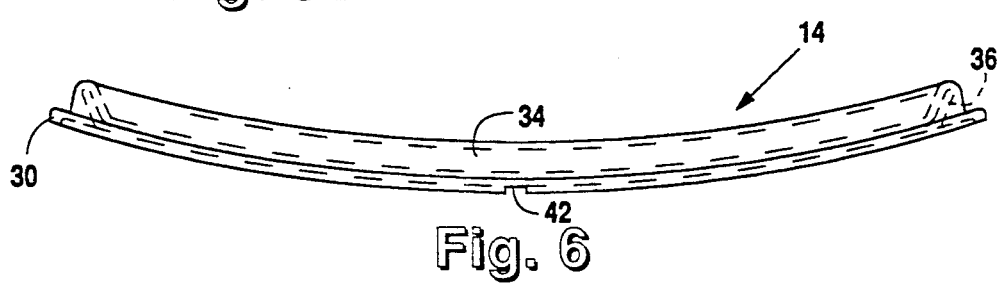
FIG. 6 is a side elevational view of the lid of FIG. 3.

By reference to FIGS. 4 and 5A and a comparison of those figures to FIGS. 6 and 5B, it can be seen that the angle of the cavity 36 in the thickened portion 34 relative to the flat surface of the recessed portion 30 of lid 14 is smaller at the ends of the oval than along the sides 28 of the oval, e.g., along the long axis thereof. Also, by reference to FIG. 6, it can be seen that lid 14 is symmetrical along a transverse axis, e.g., that the two ends of the oval are mirror images of each other. In other words, the angle of cavity 36 relative to the flat surface of the recessed portion 30 of lid 14 is the same at both ends of the oval shaped lid 14 in spite of the function of cavity 36, e.g., receiving the flare 32 having a variable pitch. This apparent anomaly in the pitch of flare 32 and the angle of cavity 36 (different at the two ends 22 and 24 of cup 12 but the same at both ends of lid 14) is the result of the combination of the difference in pitch of the flare 32 at the respective ends 22 and 24 of cup 12, the concave surfaces 26 of the rim 20 of cup 12, and the outward draft of the upstanding sidewall 18 from bottom 16 to top. The curve in the rim 20 along the sides of the oval-shaped cup 12 requires a smaller pitch in the outward flare 32 relative to the sidewall 18 at the high end 22 of cup 12 than the low end 24 while the angle of that flare 32 relative to the radius of the curve of the concave surface 26 is, as demonstrated by the angle of the cavity 36 at both ends of the curved lid 14, the same. Coincidentally, the outward flare 32 functions to retain the lid 14 on cup 12 when received within cavity 36.

Also contributing to the water-tight seal is the material from which lid 14 is molded, a resilient plastic such as a high density polyethylene being preferred. As shown in FIG. 3, the recessed portion 30 of lid 14 is provided with one or more scores, or portions of reduced thickness, 42 to facilitate perforation of lid 14 for withdrawing a sample from the closed specimen container without removing the lid 14 from cup 12.

Figure 7:
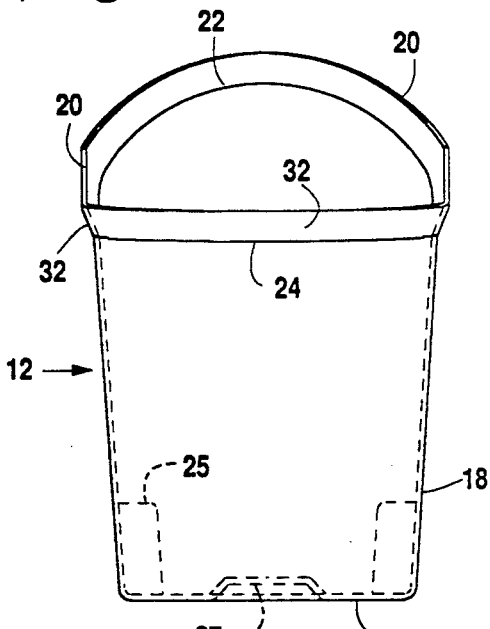
FIG. 7 is a side elevational view of the cup of FIG. 1.

Although preferably comprised of a fairly rigid material such as high density polypropylene, the bottom 16 of cup 12 may be provided with an indentation 27 to impart additional rigidity to the cup along the long axis of the oval shape thereof. As best shown in FIGS. 1 and 7 and discussed above, the upstanding sidewalls 18 of cup 12 are provided with a slight outward draft from bottom 16 to the rim 20 at the top to enable the cup 12 to be stacked, or nested, one within the other for ease in transportation and decrease storage space. Stacking pins 25 are molded in the wall 18 of each cup 12 to prevent the cup 12 from nesting too tightly. A plurality of cups 12', 12'', 12''', etc., having the respective rims 20', 20'', 20''', etc., are shown in FIG. 9 for purposes of demonstration.

Although the present invention has been described by referring to a presently preferred embodiment thereof, it will be understood by those skilled in the art who have the benefit of this disclosure that a number of changes can be made to that preferred embodiment without departing from the manner in which the various elements comprising that embodiment function to achieve the stated results. For instance, the oval-shaped cup 12 need not to be provided with a high side 22 and a low side 24 to enable the cup 12 to be used successfully for collection of urine from a female patient; the configuration of cup 12 in this manner simply provides greater convenience in the use thereof. Further, the pitch of flare 32 (and the angle of cavity 36) need not be limited to the angles set out herein; all that is required is that flare 32 be angled outwardly enough to insure that the outer surface of flare 32 will be engaged by the elbow 38 of the thickened portion 34 of lid 14 around rim 20 to insure a water-tight seal therebetween and that lid 14 is retained thereon. All such changes, and other obvious modifications thereof, are intended to fall within the spirit and scope of the following claims.

What is claimed is:

1. An anatomically designed urine collection and specimen container for use by female patients comprising:
    a cup formed of a bottom and an upstanding sidewall surrounding said bottom and having an oval shape when viewed from above, said sidewall terminating in a rim having concave surfaces along the sides of the oval for approximating the contour of the external genitalia of a female patient from whom a urine specimen is to be collected and having one end higher than the other;
    an outward flare formed at an obtuse angle relative to the sidewall around the rim of said cup the obtuse angle being higher at the high end of the cup than at the low end of the cup;
    an oval-shaped lid comprised of a recessed, interior portion forming a flat surface for covering said cup and a thickened portion around the edges thereof, the thickened portion having a cavity formed therein at an angle relative to the flat surface of the recessed portion of said lid for receiving said flare when said lid is applied to the rim of said cup; and
    the pitch of said outward flare at one end of the oval-shaped cup being higher than the pitch of said outward flare at the other end of said oval-shaped cup.

2. The specimen container of claim 1 wherein the portions of the rim of said cup forming the sides of the oval are concave and the portions of the rim of said cup forming the ends of the oval are flat.

3. The specimen container of claim 1 wherein said lid is provided with a portion of reduced thickness for facilitating perforation of said lid for withdrawing a sample from said cup while said cup is closed by said lid.

4. The specimen container of claim 1 wherein said lid is provided with an elbow for sealing against the outside surface of the flare formed at the rim of said cup when said lid is applied to said cup.

5. The specimen container of claim 4 wherein said lid is comprised of a resilient material causing said elbow to be biased against the outside surface of the flare to exert approximately equal pressure all the way around the rim of said cup so as to effect a water-tight seal with said cup.

6. The specimen container of claim 1 wherein said lid is symmetrical along the transverse axis thereof for receiving said outward flare at either the higher or the lower end of said oval-shaped cup in the cavity formed at either end of said oval-shaped lid.

7. A urine collection and specimen container for use by female patients which is shaped to facilitate collection of a urine specimen by a female patient and is water-tight comprising:
    a cup formed of a bottom and an upstanding sidewall which is generally oval-shaped when viewed from above;
    the rim formed by the upstanding sidewall at one end of said oval-shaped cup being higher than the rim at the other end and being concave along the sides of said cup for approximating the contour of the external genitalia of a female patient from whom a urine specimen is to be collected;
    a flare formed along the rim of said cup at an angle relative to the sidewall of said cup;
    a generally oval-shaped lid having a cavity formed around the edges thereof for receiving said flare therein and a flat surface for covering said cup when said lid is applied to the rim thereof, the cavity being formed at an angle relative to the flat surface of said lid, the angle of the cavity relative to the flat surface being the same at both ends of said oval-shaped lid whereby either end of said lid can be applied to either the high or the low end of said oval-shaped cup; and
    the angle of said flare relative to the sidewall of said cup being higher at the high end than the angle at the other end of said cup so as to form a water-tight seal when received in the cavity formed in said lid.

8. The container of claim 7 wherein said flare is formed at an obtuse angle relative to the sidewall of said cup.

9. The container of claim 7 wherein said lid is comprised of a resilient plastic.

10. The container of claim 7 wherein said lid is curved along the long axis thereof to facilitate application of said lid to the rim of said cup along the concave rim of said cup.

* * * * *